United States Patent [19]

Kamachi et al.

[11] 4,176,376
[45] Nov. 27, 1979

[54] IMAGE PROCESSING SYSTEM

[75] Inventors: Shinichi Kamachi, Hino; Masao Izawa, Hachioji; Nagahiro Gocho, Hachioji; Yoshio Nakajima, Hachioji; Shinichiro Hattori, Tokyo, all of Japan

[73] Assignee: Olympus Optical Company Limited, Tokyo, Japan

[21] Appl. No.: 919,716

[22] Filed: Jun. 27, 1978

Related U.S. Application Data

[63] Continuation of Ser. No. 739,051, Nov. 5, 1976, abandoned.

[30] Foreign Application Priority Data

Nov. 10, 1975 [JP] Japan ................................ 50/134837

[51] Int. Cl.$^2$ .............................................. H04N 7/02
[52] U.S. Cl. ................................ 358/107; 235/92 PC
[58] Field of Search ................... 358/93, 96, 106, 107; 235/92 PC

[56] References Cited

U.S. PATENT DOCUMENTS

| 3,579,249 | 5/1971 | Dewey et al. | 358/107 |
| 3,674,926 | 7/1972 | Dewey et al. | 358/107 |
| 3,811,036 | 5/1974 | Perry | 358/107 |
| 3,978,324 | 8/1976 | Rayner | 358/107 |

Primary Examiner—Robert L. Richardson
Attorney, Agent, or Firm—Toren, McGeady and Stanger

[57] ABSTRACT

An image processing system converts gradation data of an image signal from a television camera into a digital code and transfers it to a computer. In the image processing system suitable means slice a portion which contains data of the image signal at a given level, means quantize a signal waveform obtained by the slice means, means count how many numbers of pulses obtained by the quantizing means at a given portion of one horizontal scan during each horizontal scan, and means for transfer counted values of the counting means to the computer at every completion of one horizontal scan.

5 Claims, 6 Drawing Figures

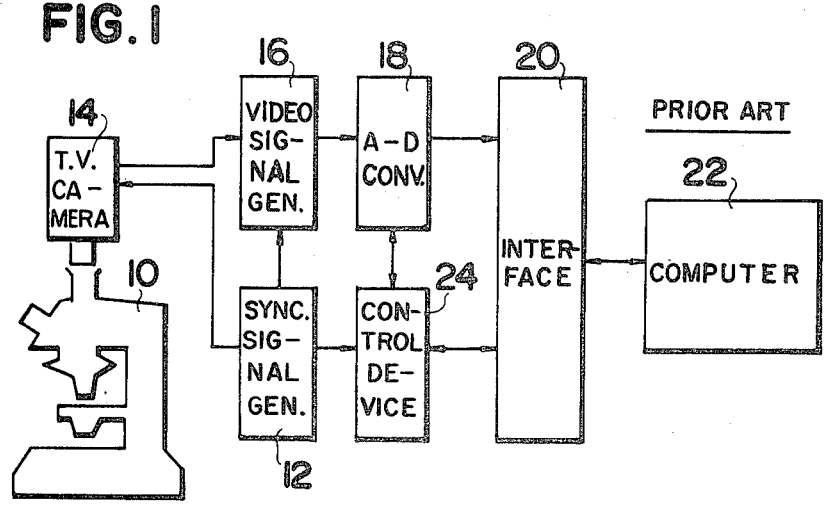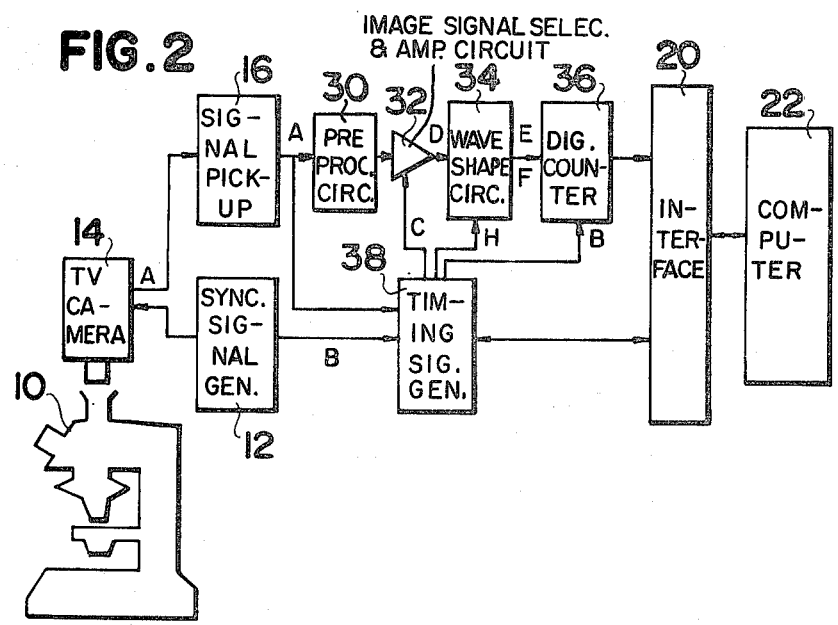

IMAGE PROCESSING SYSTEM

This is a continuation of application Ser. No. 739,051, filed Nov. 5, 1976 and now abandoned.

BACKGROUND OF THE INVENTION

1. Field of the Invention

The present invention relates to an image processing system, particularly for converting information concerning gradation variation of a television image into a digital code and transmitting it to a computer.

2. Description of the Prior Art

Generally, in carrying out a morphological study on systems, cells or the like, an image observed by a microscope is picked up by a television camera (hereinafter referred to as TV camera), and the optical densities of the various portions of the microscope image, i.e., a gradation of an image of the system or cell, is coded from its video signal and read in a memory of the computer. A pattern having more than a given optical density is counted, or the ratio of optical densities is sought and the like, and any treatment in accordance with the purpose is carried out by a computer, and a result thereof is derived from the computer in general.

In conventional image processing systems, a TV camera scans the image field and the momentary densities are stored for processing in a computer. With a TV camera using the NTSC system, the subdivisions per screen are about 500 in the horizontal direction and about 500 in the vertical direction. The number of subdivisions coded is then 250,000. If the data for the optical density of one image element is composed of six bits, the total data which must be stored by a computer equals 1.5 times $10^6$ bits. For this purpose a computer must have a very large memory. Moreover, the time for a single horizontal scan in an NTSC TV camera is 63.5 microseconds. Five hundred image elements are subdivided within this time period. Therefore, the various circuits, such as the sample and hold circuit, the analog-to-digital converters, and the like, which process this information, must have very fast time constants. Accordingly, because of the large memory needed by the computer and the necessary high speed components, conventional image processing systems are expensive.

For performing morphological analyses, such as for analyzing samples of cells, systems, and the like, or non-organic samples such as metallic materials, a more effective analysis might be achieved by noting the sample's special texture, optical density variations, and the like. For example, for observing a live cell, system, or the like, with a microscope, such a sample may be treated optically as a phasic body. A phase difference microscope may observe the image input. In some cases it may be preferable to treat the analysis on the basis of the optical density changes, the number of changes, and the like instead of the optical density of the whole image. However, even when considering the change magnitudes of the optical densities of an optically phasic body, it is necessary to use an expensive and complicated imaging processing system. All the optical densities must be supplied to the computer.

An object of the present invention is to eliminate the aforementioned defects of conventional systems.

Another object of the invention is to furnish improved image processing systems.

SUMMARY OF THE INVENTION

According to a feature of the invention, these objects are attained in whole or in part, by slicing a portion of the image information of an image signal from a television camera at a predetermined level, quantizing a waveform of the signal obtained by the slicing means, counting the number of pulses obtained by the quantizing means during every horizontal scan, and transferring the counted values of the counting means to a computer at every completion of one horizontal scan, all with suitable means.

The invention provides an improved image processing system in which a number of optical density changes within a predetermined scanning period are counted and transferred to the computer. This contrasts with coding all of the optical densities of the image elements of the television image. It involves treating only optical density variation magnitudes as when measuring the density of, for example, an optically phasic body.

These and other features of the invention are pointed out in the claims. Other objects and advantages of the invention will become evident from the following detailed description when read in light of the accompanying drawings.

BRIEF DESCRIPTION OF THE DRAWINGS

FIG. 1 is a block diagram showing a conventional image processing system;

FIG. 2 is a block diagram showing one embodiment of the image processing system according to the present invention;

DESCRIPTION OF PREFERRED EMBODIMENTS

Figure 3:
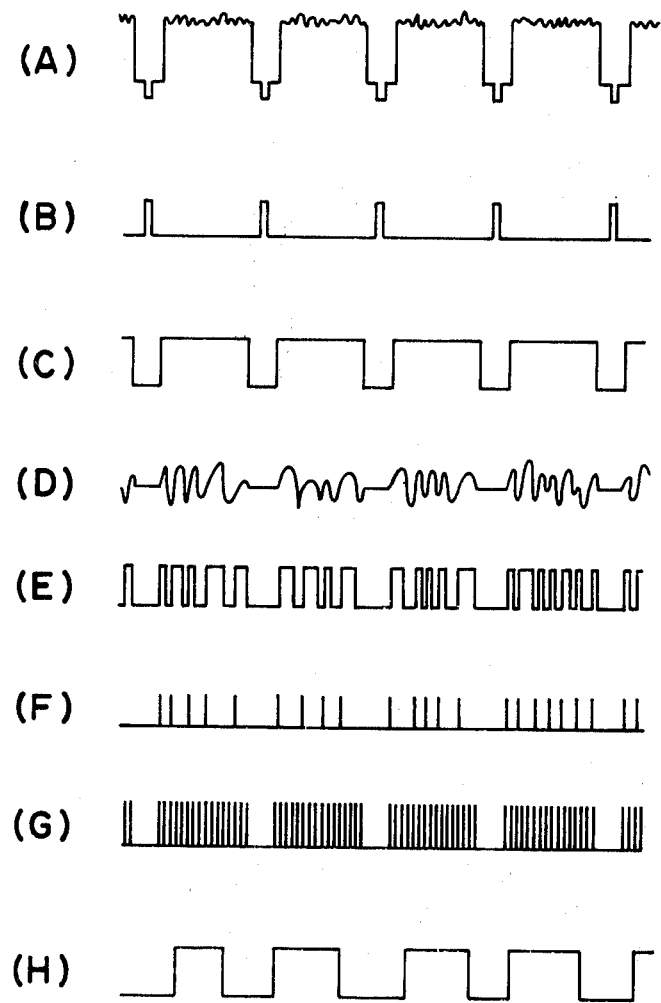
FIG. 3 is a signal waveform diagram explaining the operation of the image processing system shown in FIG. 2.

FIG. 1 shows a block diagram illustrating one embodiment of a conventional image processing system. Here a microscope image of a system or a cell sample obtained by a microscope 10 is converted into an electric video signal by a TV camera 14 which receives horizontal and vertical synchronizing signals from a synchronizing signal generator generating device 12. The thus converted video signal is supplied to an analog-digital converter 18 (hereinafter referred to as an A-D converter) through a video signal taking up device 16 and divided into a plurality of levels with respect to each optical density thereof and converted into digital codes, and then supplied to a computer 22 through an interface 20.

A timing signal from the synchronizing signal generating device 12 is supplied as a synchronizing signal to the video signal taking up device 16 and also supplied to a control device 24. The timing signal is treated as a signal showing the positional co-ordinates of a visual field of the TV camera 14. At the same time it is utilized for controlling the timing of a sample and hold of the A-D converter 18 and data take-up timing or the like by the computer 22 through the interface 20. The control device 24 receives an order in response to the special purpose along with an image taking up program from the computer 22 through the interface 20 and acts for determining each of the above timings. Thus, the computer 22 successively reads the optical density of an optional position of an image from the TV camera into the memory under the mutual control with the control device 24 in accordance with a given program. In general, the scanning of the X-coordinates and Y-coordinates of the microscope image is carried out by the TV camera 14. All the optical densities of television images obtained by the TV camera 14 are coded to be read in the memory of the computer 22. Then, as described above, patterns having more than a given optical density are counted or an operation for seeking the surface ratio by the optical density is carried out by a computer. In order to code the optical density of the television image, it is necessary to subdivide a screen. Generally, with a TV camera using the NTSC system, the subdivision per screen is about 500 in the horizontal direction (X) and about 500 in the vertical direction (Y), i.e., $500 \times 500 = 250,000$ to code the optical density of each image element and transmit it to the computer.

In such a conventional image processing system, if the data for the optical density of one image element is composed, for example, of 6 bits, the total data in one screen becomes enormous, such as $6 \times 250,000 = 1.5 \times 10^6$ bits. Thus a computer having a very large memory capacity is required. Further, the time for one horizontal scan of the TV camera is 63.5 micro seconds with the NTSC system, so that about 500 image elements are sub-divided within this time. Therefore, a sample and hold circuit, an analog-digital converting circuit and the like should be operated very quickly. Such operation is very difficult. Accordingly, because the computer must have a large memory capacity and use of high speed components, a conventional image processing system is very expensive.

One embodiment of an image processing system according to the present invention is shown in FIG. 2. Here, like reference characters refer to like members or devices in FIG. 1. An image from a microscope 10 is converted into a common television image signal shown in FIG. 3A by a TV camera 14, a synchronizing signal generator or generating device 12 and a video signal pickup device 16 and transmitted to a pre-processing circuit 30. The pre-processing circuit 30 performs extraction, differential and the like, of the frequency components extraneous to the image signal, if necessary. Hence if the circuit 30 extraneous is used, for example, as a differential circuit having a small time constant so that only the high frequency component is taken out at the output terminal. The image signal optionally treated by the pre-processing circuit 30 is converted into a signal containing only the image information component, exclusive of the synchronizing signal and the like. The image signal is then amplified and supplied to a wave shaping circuit 34 as a signal having the waveform shown in FIG. 3D. This wave shaping circuit 34 produces a rectangular wave shown in FIG. 3E by quantizing the signal shown in FIG. 3D above a certain threshold level and converts the result into pulse signals shown in FIG. 3F. The thus obtained pulse signals correspond to the number of optical density changes and are supplied to a digital counter 36 to count the number of pulses. The counted value of the digital counter 36 is supplied to the computer 22 through the interface 20 and successively read in the memory of the computer 22. In FIG. 2, a timing signal generating circuit 38 supplies each kind of gate signal and an interrupt pulse to the interface by utilizing the timing signals from the synchronizing signal generator 12 and the synchronizing signal (FIG. 3B) separated from the image signal from the video signal pick-up 16. The image signal selection and amplifying circuit 32 receives, from the circuit 38, a gate signal shown in FIG. 3C and corresponding to to the signal period of the image information component of the image signal. To the wave shaping circuit 34, circuit 38 supplies a gate signal shown in FIG. 3H for taking up the optional portion of one horizontal scan. To the digital counter 36, circuit 38 supplies a reset signal (horizontal synchronizing signal shown in FIG. 3B). Accordingly, digital counter 36 counts a pulse number from wave shaping circuit 34 under the control of a gate signal from timing signal generating circuit 38. At the completion of one horizontal scan, an interrupt pulse is simultaneously transmitted from the circuit 38 to the interface 20, so that the counted value of the digital counter 36 at every horizontal scan is transmitted to the computer.

A pulse signal shown in FIG. 3G is a clock pulse synchronized with the gate signal shown in FIG. 3C. This clock pulse times the image information component in the image signal. Accordingly, the clock pulse is counted at every horizontal scan to generate a gate signal in the period of an optional counted value only. If this value is utilized as a gate signal for the digital counter 36, a gate signal for removing the optional portion of one horizontal scan can be obtained. That is, when a gate signal for the digital counter 36 is formed as described above, and the counting is carried out by this gate signal, a special position in all horizontal scanning lines of about 500 is noted and the amount of the optical density change for this position can be obtained. Such a gate signal can take out an optional portion, i.e., region, of one horizontal scanning, so that it is referred to as a region gate signal hereinafter. In the embodiment shown in FIG. 2, this region gate signal is formed by the timing signal generating circuit 38, but it can be also formed by a circuit shown in FIG. 4.

Figure 4:
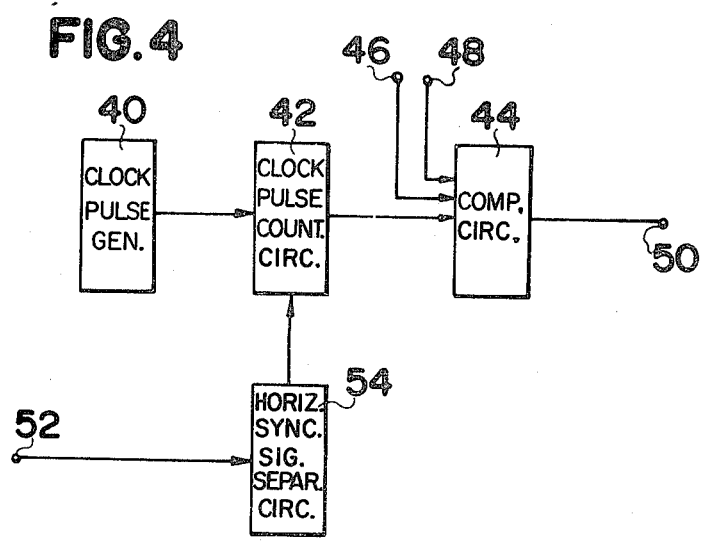
FIG. 4 is a block diagram showing a circuit for obtaining a region gate signal.

In FIG. 4, reference numeral 40 represents a clock pulse generator, 42, and a clock pulse counting circuit for counting clock pulses from the clock pulse generator 40. A comparison circuit 44 compares the counted value of the clock pulse counting circuit 42 with the inputs of the region upper limit value and the region lower limit value through terminals 46 and 48. Circuit 44 operates a given output until the counted value of the clock pulse counting circuit 42 agrees to the region upper limit value from the point where the counted value of the circuit 42 agrees to the region lower limit value. Numeral 50 represents an output terminal, 52 an image signal input terminal for receiving an image signal from the video signal take up device 16 shown in FIG. 2. Numeral 54 represents a horizontal synchronizing signal separating circuit for separating the horizontal synchronizing signal from the image signal and supplying the thus separated synchronizing signal as a reset signal to the clock pulse counting circuit 42. According to such construction, the clock pulse counting circuit 42 counts clock pulses from the start point of the horizontal scanning and is reset by the following horizontal synchronizing signal. When the counted value of the clock pulse counting circuit 42 is positioned between the region lower limit value and the region upper limit value, and if a given output is obtained from comparison circuit 44, the region gate signal for removing the optional portion of each horizontal scanning shown in FIG. 3H is obtained at output terminal 50. The region lower limit value and the region upper limit value are set at every horizontal scan in accordance with the program of the computer 22 and supply the terminals 46 and 48 through the interface 20.

Figure 5:
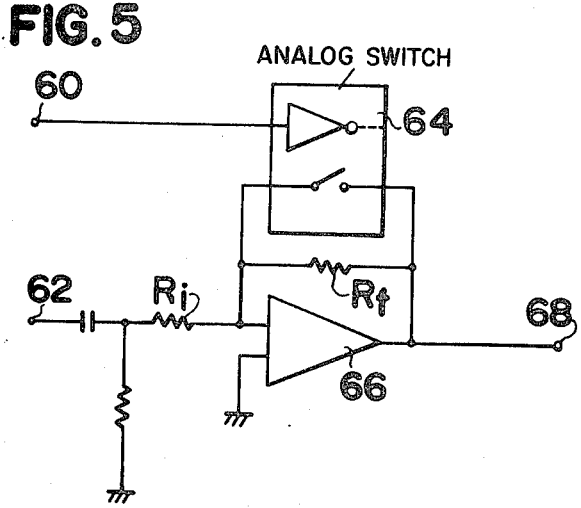
FIG. 5 is a block diagram showing a circuit for obtaining a signal only in the image information component from the image signal.

An example of the image signal selection and amplifying circuit 32 shown in FIG. 2 appears in FIG. 5. In FIG. 5, reference numeral 60 represents a gate signal input terminal connected to the timing signal generating circuit 38 (FIG. 2). Numeral 62 represents an image signal input terminal connected to the output of preprocessing circuit 30 (FIG. 2). Numeral 64 represents an analog switch which is switched on or off by the gate signal, and 66, an amplifer connected to an input resistor $R_i$ and a feedback resistor $R_f$. The analog switch 64 is connected across the feedback resistance $R_f$, so that while an input is supplied to the terminal 60, the switch 64 is open, and while the input is not supplied thereto, it is closed and short-circuits the feedback resistance $R_f$. Accordingly, the amplifier 66 operates as an amplifier having an amplification $R_f/R_i$ when the analog switch 64 is off, while the amplification becomes 0 (that is, the output is 0) when the analog switch is on. Therefore, when a gate signal shown in FIG. 3C is supplied to gate signal input terminal 60, the image signal supplied to the terminal 62 is amplified in the image information component only, so that the signal shown in FIG. 3D is obtained at the output terminal 68. Extracting the image information component from the image signal shown in FIG. 3A, may be accomplished by switching a feedback system such as shown in FIG. 5, a method of switching an output system or an input system, and the like.

Figure 6:
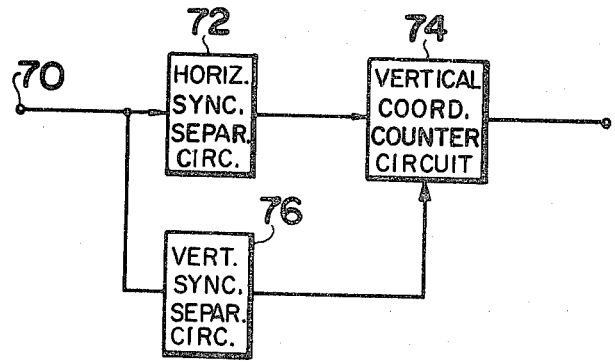
FIG. 6 is a block diagram showing a circuit for obtaining a coordinate value signal in the vertical scanning direction (Y-axial direction).

Further, the coordinate value in the Y-direction (vertical scanning direction) can be defined by, for example, a circuit shown in FIG. 6. That is, the image signal from the video signal pick up device 16 (FIG. 2) is supplied to a horizontal synchronizing separation circuit 72 from a terminal 70 to form a horizontal synchronizing signal. This signal is then counted by a vertical coordinate counting circuit 74. If the counting circuit 74 is reset by a vertical synchronizing signal derived from the image signal by a vertical synchronizing separation circuit 76, the vertical coordinate counting circuit 74 counts a number of horizontal scans at every vertical synchronizing signal so that the coordinate value in the Y-direction can be obtained. Further, the pre-processing circuit 30 is provided, if necessary, but if a differential circuit having a small time constant is used as this preprocessing circuit 30 as described above, only the optical density change of the high frequency component can be extracted. Then if the focus of the TV camera is controlled so that a number of optical density changes, i.e., the counting value of the digital counter 36 is made the maximum, an automatically focused system can be constructed. Further, with respect to the analog component of an image signal, if the slice level is suitably selected, any foreign matter having abnormally high optical density can be detected.

The image processing system according to the present invention has the aforementioned construction so that as a circuit construction, a sample and hold circuit, an AD converting device, a control device and the like which are expensive analog processing elements are not required. The invention can be composed of only a technically simple and cheap image selection and amplifying circuit, quantizing circuit (Shmitt trigger circuit), counting circuit and timing signal generating circuit, and thus it becomes possible to allot sufficient time such as 63.5 microsecond per data to transfer data to the computer. Further, the data number to be read in is compressed to 525 as the number of horizontal scans, so that the reading time can be sped up, and the processing program of the computer becomes very simple. Accordingly, the present invention can provide a very cheap image processing system in both the hard- and soft-wares.

What is claimed is:

1. An image processing system, comprising a microscope for observing a sample, a television camera optically coupled to the microscope for converting the microscope image of the sample into electric image signals, an image signal pickup device connected to the camera for extracting a required part of the image signals, a synchronizing signal generator connected to the camera and to said pickup device for generating synchronizing signals for the image signal pickup device, a preprocessing circuit connected to the image signal pickup device for extracting and differentiating a frequency component of the image signal and detecting the number of optical density changes, an image signal selection and amplifying circuit connected to the preprocessing circuit for selecting and amplifying the component of the image signal, a wave shaping circuit connected to the image signal selection and amplifying circuit for quantizing the image information component to obtain a train of rectangular pulses, a digital counter connected to the wave shaping circuit for counting the number of the rectangular pulses and a computing device for memorizing the number of optical density changes and effecting the processing of the image.

2. An image processing system as claimed in claim 1, further comprising a timing signal generating circuit connected to said synchronizing signal generator and said pickup device as well as said selection and amplifying circuit and said wave shaping circuit and said computing device to receive synchronizing signals from the synchronizing signal generator and image signals from the image signal pickup device and for generating gate signals to the image signal selection and amplifying circuit and the wave shaping circuit, and the reset signals to the digital counter for counting the number of optical density changes in an arbitrary section of the image.

3. An image processing system as claimed in claim 2, wherein the timing signal generating circuit comprises a clock pulse generator, a clock pulse counter connected to said generator for counting clock pulses therefrom, a comparator connected to the counter for comparing the counted value of the clock pulse counting circuit with the inputs of the region upper limit value and the region lower limit value and generating an output until the counted value of the clock pulse counting circuit agrees with the upper limit value from the point where the counted value of the counting circuit agrees to the lower limit value, and a horizontal synchronizing signal separating circuit connected to the image signal taking up device for separating a horizontal synchronizing signal from the image signal whereby any portion of one horizontal scanning can be extracted.

4. An image processing system as claimed in claim 1, wherein the preprocessing circuit consists of a differentiating circuit.

5. An image processing circuit as claimed in claim 1, wherein the image signal selection and amplifying circuit comprises an analog switch connected to the timing signal generator for selecting the information component of the image signal and an amplifier connected to the preprocessing circuit and the analog switch and having an input resistance and a feedback resistance for amplifying the selected information component of the image signal.

* * * * *